United States Patent [19]
Giebner

[11] Patent Number: 5,932,811
[45] Date of Patent: Aug. 3, 1999

[54] PORTABLE FOAM COMPRESSION TESTER

[75] Inventor: Christopher S. Giebner, St. Peterburg, Fla.

[73] Assignee: Comten Industries, Inc., Pinellas Park, Fla.

[21] Appl. No.: 09/098,483

[22] Filed: Jun. 16, 1998

[51] Int. Cl.[6] .................................................. G01N 3/08
[52] U.S. Cl. ............................................................. 73/818
[58] Field of Search ............................. 73/818, 821, 823, 73/824, 790

[56] References Cited

U.S. PATENT DOCUMENTS

| | | | |
|---|---|---|---|
| 3,786,676 | 1/1974 | Korolyshun et al. | 73/818 X |
| 3,975,950 | 8/1976 | Erdei | 73/790 |
| 4,377,089 | 3/1983 | Shanks | 73/818 |
| 4,393,716 | 7/1983 | Clark et al. | 73/818 |
| 5,044,193 | 9/1991 | Fudacz | 73/818 |
| 5,067,353 | 11/1991 | Sersen | 73/849 |
| 5,251,492 | 10/1993 | Nowag | 73/862.472 |

*Primary Examiner*—Elizabeth L. Dougherty

[57] ABSTRACT

A portable foam compression tester for the testing of compressive yield strengths of roofing foam on-site at the point of foam application. The portable foam compression tester system comprises of a foam compression fixture attached to a standard roofing pullout tester common in the industry. The foam compression fixture consists of four support feet which, at one end, fix the foam compression fixture to the standard roofing pullout tester. A lift bar is attached to the pulling mechanism of the standard roofing pullout tester and pulls a moving platen upward as the tester is operated. A foam sample is placed on the moving platen and the sample is compressed against a fixed platen. The force required for compression of the foam sample is indicated on the force readout of the standard roofing pullout tester.

8 Claims, 2 Drawing Sheets

PORTABLE FOAM COMPRESSION TESTER

BACKGROUND OF THE INVENTION

1. Field of the Invention

This invention relates to portable compression testing of polyurethane or similar roof insulating and building materials to determine the yield point of a known size core sample in the field.

2. Description of the Background Art

In building construction, it is common practice in the industry to use spray foam to insulate and coat roofs. This spray foam is applied to the roof in a liquid state and expands to set up as foam very quickly. The end product is a porous cellulose foam that must meet certain yield point guidelines established by the industry. These guidelines are set to protect the integrity of the roof from events such as hail, wind, foot traffic, equipment loading, and other common occurrences.

In addition, the material is to be tested from a sample that has been sprayed at the point of application (i.e. on the roof). This will take into account the liquid foam mixture used for the specific application and environmental conditions existing for the specific location.

Presently, the only method of testing foam being applied at a specific site is to spray a sample on site and send these samples to a laboratory for testing. These tests normally take anywhere from 1 to 5 days. Common practice is to coat the entire roof or application area before the test results are returned. This saves time which is very valuable in the construction industry. However, if the test results show that the foam failed to meet certain guidelines, then all of the foam applied must be removed and the roof must be redone. This is a very costly procedure that wastes both time and money.

Currently, there are portable, on-site testers on the market that test the pull-out strength of roofing fasteners such as nails and screws. There are also testers considered portable that can measure the deflection, or compression distance, of materials such as foam used in bedding. Another portable tester can be mounted to roof supports and measure the force it takes to deflect the roof membrane material.

Some of these representative testers are disclosed in U.S. Pat. Nos. 4,753,115; 3,942,368; 3,563,087; 4,662,227; 4,004,457; and 5,067,353. The disclosures of which are hereby incorporated by reference herein. While all of the testers listed above can provide for portable testing of construction building materials, none can test for the compressive yield strength of spray roof foam or foam building materials on-site at the point of application.

Therefore, it is the object of this invention to provide a method of testing for the compressive yield stress of spray roof foam of foam building materials.

Another object of the invention is to provide a compression foam tester that is portable and can be used on-site at the point of application.

Another object of the invention is to provide a compression foam tester that is simple to set-up and easy to use.

Another object of the invention is to provide a compression foam tester that can be used in conjunction with, and adapted to, the many portable construction fastener testers on the market.

The foregoing has outlined some of the pertinent objects of the invention. These objects should be construed to be merely illustrative of some of the more prominent features and applications of the intended invention. Many other beneficial results can be obtained by applying the disclosed invention in a different manner or by modifying the invention within the scope of the disclosure. Accordingly, other objects and a more comprehensive understanding of the invention may be obtained by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention comprises of a fixture for the portable compression testing of spray foam or similar products used in the roofing industry. When attached to a standard roofing pullout tester, the portable compression tester will provide a method for determining the yield strength of various roofing foams. The tester is comprised generally of a fixed platen and a moving platen where the foam sample is placed in-between and compressed. The foam sample is cut from a test section of foam applied on-site using a core cutter or similar device. Attached to the fixed platen are support feet that allow the fixture to be set on the roof or any solid surface during testing. The opposite ends of the support feet extend through the fixed platen and are used to attach to the frame of the pullout tester being used. The moving platen is attached to a lifting bar with draw rods the slide through the fixed platen. This lifting bar is connected to the pulling end of the pullout tester. As the pullout tester is operated, it will pull the moving platen upward toward the fixed platen, compressing the foam sample that has been placed on the moving platen. The foam is compressed until the force as read on the gauge readout ceases to increase wherein the yield point is reached and the test is finished.

An important feature of the present invention is that the portable compression tester facilitates obtaining accurate yield strengths of roofing foam and related products at the point of application rather than having to transport the samples to remote labs for similar testing.

Another important feature of the present invention is that the portable compression tester is a fixture that can be mounted to existing pullout testers common in the marketplace with minimal modification.

The foregoing has outlined rather broadly, the more pertinent and important features of the present invention. The detailed description of the invention that follows is offered so that the present contribution to the art can be more fully appreciated. This forms the subject of the claims of the invention. It should be appreciated by those skilled in the art that the conception and the disclosed specific embodiment may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more succinct understanding of the nature and objects of the invention, reference should be directed to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
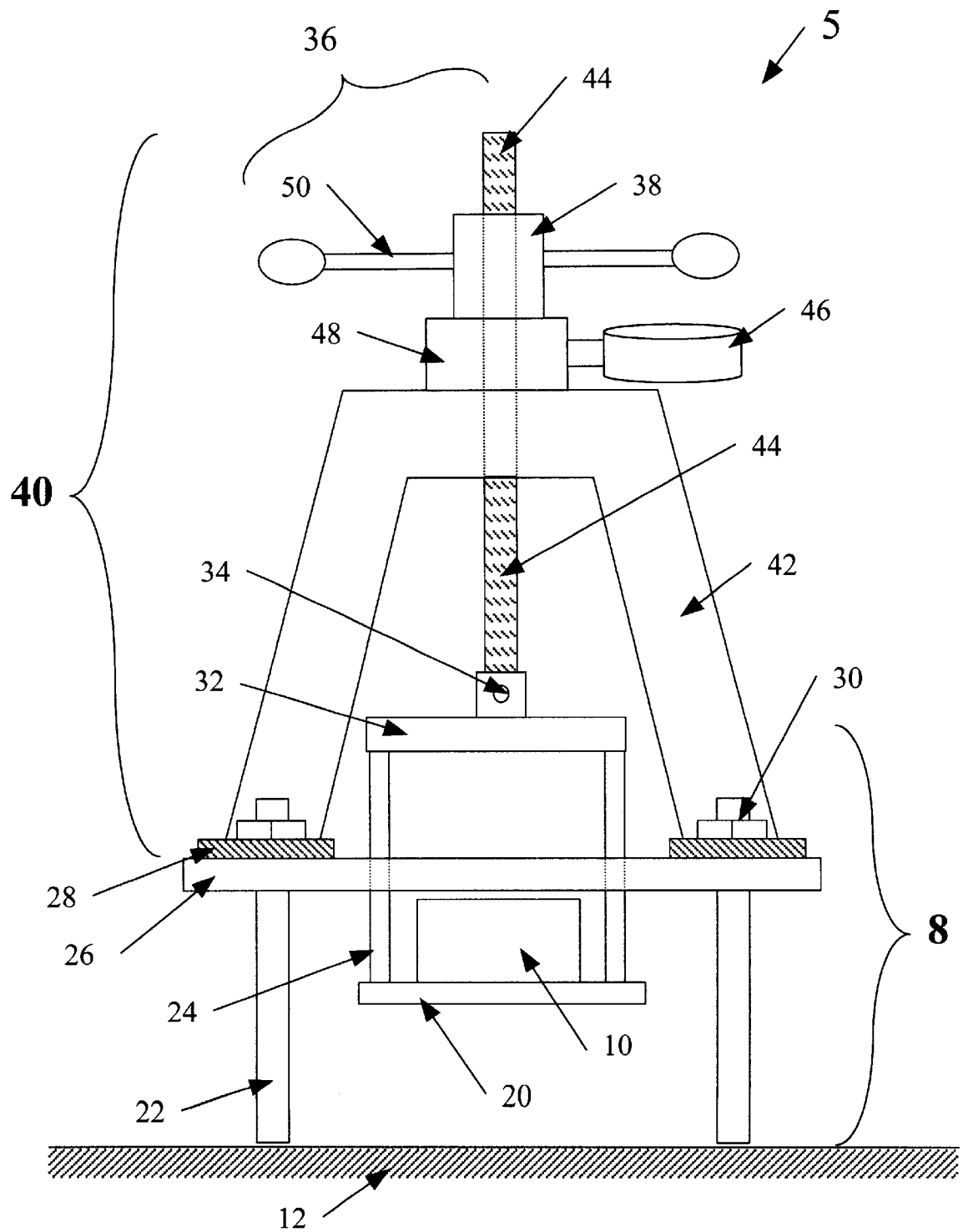
FIG. 1 is a frontal assembly view of the portable foam compression tester assembly of the present invention illustrating a existing pullout tester connected to the foam compression tester fixture including the test frame, lifting means, load readout, support feet, moving and fixed platens, and test sample in their relative positions to each other.

As shown in FIG. 1, the portable foam compression tester system 5 of the present invention can be seen in a frontal view. The portable foam compression tester system 5 can be seen to include a fastener tester assembly 40 and a foam compression fixture 8. The fastener tester assembly 40 consists of a driving means 36, force readout 46, support legs 42, and stabilizing feet 28. This is common device in the roofing industry that contains, in some form, all of the aforementioned components. The driving means 36 consists of a power screw 44 that can be translated vertically by rotating a power nut 38. The power nut can be rotated manually by capstan arms 50 or optionally with a motorized unit. Either option is commonly available in this industry. The force readout 46 can be either digital or analog and displays the force exerted by the driving means 36 on the load cell 48 through the power screw 44 in the upward direction.

The foam compression fixture 8 is an adaptable accessory and can be mounted to many fastener tester assemblies 40 utilizing the stabilizing feet 28 on the fastener tester assembly 40. The foam compression fixture 8 is attached to the stabilizing feet 28 using four mounting nuts 30. The mounting nuts 30 are threaded onto the upper end of the support feet 22. These support feet 22 form the legs that the portable foam compression tester system 5 will utilize. The support feet are permanently attached to a fixed platen 26 at the four corners. The fixed platen 26 is made out of suitable material so as it will not deform when force is applied against it from the bottom by the sample 10. Two draw rods 24 extend through the fixed platen 26 via clearance holes. These draw rods 24 can freely translate vertically up and down through the fixed platen 26. At the bottom of the draw rods 24 is attached a moving platen 20. This is where the foam sample 10 is placed to be tested. The moving platen 20 must also be made out of suitable material so as it will not deform when force is applied to the sample 10 up against the fixed platen 26. The moving platen 20 must also be suitably flat and parallel with the fixed platen 26. The moving platen 20 is pulled up by the draw rods 24 with the lift bar 32. This lift bar is attached to the lower end of the power screw 44 with a pin disconnect 34. It is to be noted that various other non-permanent means of connecting the lift bar 32 to the power screw 44 can be used.

After the foam compression fixture 8 is connected to the fastener tester assembly 40 the portable foam compression tester is placed on a solid, level surface, most likely the roof test site, using the support feet 22. A foam sample 10 of know area is to be cut from a test application of the foam and placed in between the moving platen 20 and the fixed platen 26. The power screw 44 is then translated upward utilizing the driving means 36. As the power screw 44 moves upward, it pulls the moving platen 20 up via the lift bar 32 and draw rods 24. Thus the sample 10 is compressed against the fixed platen 26. As the sample 10 is compressed, force will increase as displayed on the force readout 46. As will all roofing foams and related products, the force will continue to increase until the yield point is reached. The yield point is reached when the force ceases to increase while the power screw 44 is still being translated upward and the sample 10 being compressed. At this point, the test is terminated and the point where the force leveled off and ceased to increase is noted. This value, when compared with the area of the sample, is significant in the determination of the quality of the foam.

Figure 2:
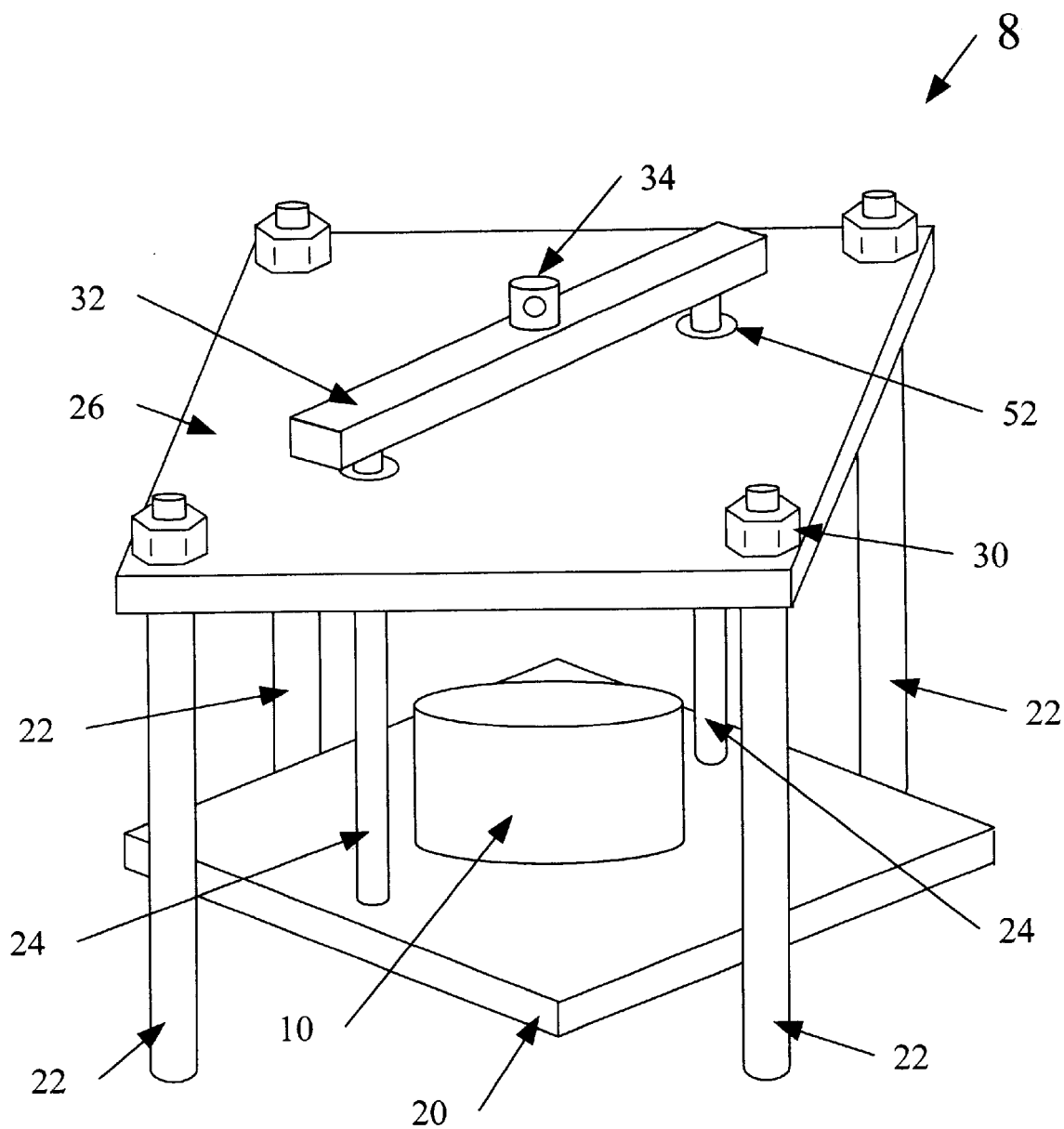
FIG. 2 is a frontal perspective view of the portable foam compression tester fixture illustrating the various parts therein including the fixed platen, moving platen, lift bar, draw rods, supports feet, and test sample in their relative positions to each other.

FIG. 2 shows a perspective view of the foam compression fixture 8. Noted are the four support feet 22 and the two draw rods 24. Also seen in this view are the clearance holes 52 that allow the lift bar 32 to pull the moving platen 20 upward using the draw rods 24.

The present disclosure includes that contained in the appended claims, as well as that of the foregoing description. Although this invention has been described in its preferred form with certain degree of particularity, it should be understood that the present disclosure of the preferred form has been made only by way of example and that numerous changes in the details of construction and the combination and arrangement of parts may be resorted to without departing from the spirit and scope of the invention.

I claim:

1. A portable foam compression tester for testing the compressive yield strength of foam roofing samples, said portable foam compression tester comprising: a compression fixture, which when attached to a standard roofing pullout tester, converts the pullout motion to a compression motion and applies a compressive force on a foam sample which is indicated on a force readout on said standard roofing pullout tester, whereby said compression fixture contains two compression platens, in between which a sample is compressed, and four support feet.

2. The portable foam compression tester as defined in claim 1 in which one compression platen is a fixed platen.

3. The portable foam compression tester as defined in claim 2 in which four support feet are attached to the said fixed platen and extend downward to stabilize the said portable foam compression tester and extend upward through the said fixed platen to attach the said portable foam compression tester to the said standard roofing pullout tester.

4. The portable foam compression tester as defined in claim 3 in which one compression platen is a moving platen.

5. The portable foam compression tester as defined in claim 4 in which two draw rods are attached to the said moving platen and extend up through said fixed platen to attach to a lift bar.

6. The portable foam compression tester as defined in claim 5 in which the said lift bar is attached to the pulling mechanism of the said standard roofing pullout tester via a detachable connector.

7. The portable foam compression tester as defined in claim 6 in which the said moving platen is pulled upward by the said lift bar and compresses a foam sample against the fixed platen.

8. The portable foam compression tester as defined in claim 1 in which the compression fixture, when attached to a standard roofing pullout tester, makes up a unit that can be easily transported and considered portable and used on-site at the point of foam application, without the need to be attached to any fixed structure for mounting or stability in order to operate.

* * * * *